United States Patent [19]

Hoelderich et al.

[11] Patent Number: 4,804,758

[45] Date of Patent: Feb. 14, 1989

[54] PREPARATION OF 1,4-DIAZABICYCLO[2.2.2]OCTANES

[75] Inventors: Wolfgang Hoelderich, Frankenthal; Kurt Schneider, Bad Durkheim; Walter Best, Weisenheim, all of Fed. Rep. of Germany

[73] Assignee: BASF Aktiengesellschaft, Ludwigshafen, Fed. Rep. of Germany

[21] Appl. No.: 105,537

[22] Filed: Oct. 8, 1987

[51] Int. Cl.[4] .......................................... C07D 487/08
[52] U.S. Cl. ..................................... 544/352; 544/351
[58] Field of Search ............................... 544/352, 351

[56] References Cited

U.S. PATENT DOCUMENTS

| | | | |
|---|---|---|---|
| 3,297,701 | 1/1967 | Brader et al. | 544/352 |
| 3,342,820 | 9/1967 | Brader | 544/352 |
| 3,956,329 | 5/1976 | Murakami et al. | 544/350 |
| 4,017,494 | 4/1977 | Bosche et al. | 260/268 T |
| 4,401,637 | 8/1983 | Marosi et al. | 423/329 |
| 4,514,567 | 4/1985 | Wells | 544/352 |

FOREIGN PATENT DOCUMENTS

| | | |
|---|---|---|
| 0046504 | 3/1982 | European Pat. Off. |
| 0069322 | 1/1983 | European Pat. Off. |
| 0034727 | 11/1984 | European Pat. Off. |
| 0158319 | 10/1985 | European Pat. Off. |
| 0158319 | 10/1985 | European Pat. Off. |
| 2434913 | 2/1975 | Fed. Rep. of Germany |
| 2442929 | 3/1976 | Fed. Rep. of Germany |
| 206896 | 2/1984 | German Democratic Rep. |

OTHER PUBLICATIONS

Nakamura Chem Abstracts, vol. 83, No. 21, Nov. 24, 1975, 17911a.

Primary Examiner—Mark L. Berch
Attorney, Agent, or Firm—Keil & Weinkauf

[57] ABSTRACT

1,4-Diazabicyclo[2.2.2]octane and C-substituted 1,4-diazabicyclo[2.2.2]octanes of the formula (I)

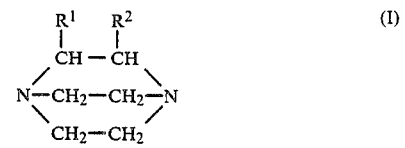

where $R^1$ and $R^2$ are each hydrogen or alkyl or alkenyl, each of 1 to 4 carbon atoms, are prepared from a heterocyclic amine of the formula (II)

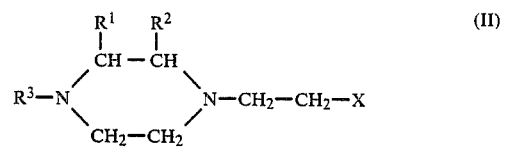

where $R^1$ and $R^2$ have the above meanings, $R^3$ is hydrogen, hydroxyethyl or aminoethyl and X is hydroxyl or amino, in the presence of borosilicate and/or iron silicate zeolites as catalysts. Particularly suitable catalysts are the borosilicate and iron silicate zeolites of the pentasil type.

5 Claims, No Drawings

PREPARATION OF 1,4-DIAZABICYCLO[2.2.2]OCTANES

The present invention relates to a process for the preparation of 1,4-diazabicyclo[2.2.2]octane (DABCO) and its C-substituted derivatives by converting a heterocyclic amine in the presence of borosilicate and/or iron silicate zeolites as catalysts.

It is known that DABCO and its derivatives can be prepared from heterocyclic amines under heterogeneous catalysis. The phosphates of Ca, Sr, Ba, Zn, La, Al, Co, Ni and Ce have been used as catalysts to date, but unsatisfactory yields have been obtained.

It is also known that aluminosilicate zeolites of the ZSM type can be used as heterogeneous catalysts for this reaction (European Pat. No. 158,319). The yields are small; although high selectivities are obtained at low conversion, low selectivities are found at high conversion. Furthermore, the reaction product contains a number of undesirable by-products, such as N-alkylpiperazines and pyrazine derivatives. The by-products have physical and chemical properties similar to those of DABCO and are therefore difficult to separate off by conventional physical methods, such as distillation and crystallization. For further processing, the purity of the DABCO has to meet high requirements, and an expensive purification procedure is therefore necessary.

It is an object of the present invention to provide catalysts which give high yields (conversion x selectivity) of the desired 1,4-diazabicyclo[2.2.2]octanes and avoid the abovementioned disadvantages.

We have found that this object is achieved, and that 1,4-diazabicyclo[2.2.2]octane and C-substituted 1,4-diazabicyclo[2.2.2]octanes of the formula (I)

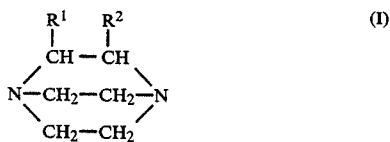

where $R^1$ and $R^2$ are each hydrogen or alkyl or alkenyl, each of 1 to 4 carbon atoms, are obtained in the desired manner, if a heterocyclic amine of the formula (II)

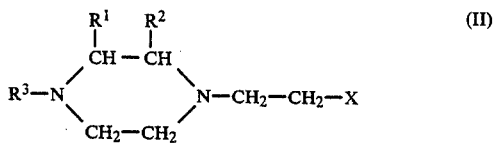

where $R^1$ and $R^2$ have the above meanings, $R^3$ is hydrogen, hydroxyethyl or aminoethyl and X is hydroxyl or amino, is converted in the presence of borosilicate and-/or iron silicate zeolites as catalysts.

Preferably, compounds such as monohydroxyethylpiperazine, dihydroxyethylpiperazine, monoaminoethylpiperazine and aminoethylhydroxyethylpiperazine can be converted according to the invention.

Zeolites are advantageously used in the acidic form as catalysts for the novel process. Zeolites are crystalline aluminum silicates which have a highly ordered structure with a rigid three-dimensional network of $SiO_4$ and $AlO_4$ tetrahedra which are linked by common oxygen atoms. The ratio of Si and Al atoms to oxygen is 1:2. The electrovalency of the aluminum-containing tetrahedra is balanced by the inclusion of cations in the crystal, for example an alkali metal or hydrogen ion. Cation exchange is possible. The voids between the tetrahedra are occupied by water molecules prior to dehydration by drying or calcination.

In the zeolites, other elements, such as B, Ga, Fe, Cr, V, As, Sb, Bi or Be, or a mixture of these, may be incorporated in the framework in place of aluminum, or the silicon can be replaced by a tetravalent element such as Ge, Ti, Zr or Hf.

These zeolites may have different chemical compositions. They are aluminosilicate, borosilicate, iron silicate, beryllium silicate, gallium silicate, chromium silicate, arsenic silicate, antimony silicate and bismuth silicate zeolites or mixtures of these, as well as aluminogermanate, borogermanate, gallium germanate and iron germanate zeolites or mixtures of these.

The borosilicate and iron silicate zeolites of the pentasil type are particularly suitable for the novel process.

Borosilicate zeolites can be synthesized, for example, at from 90° to 200° C. under autogenous pressure by reacting a boron compound, eg. $H_3BO_3$, with a silicon compound, preferably finely divided silica, in aqueous amine solution, in particular in 1,6-hexanediamine or 1,3-propanediamine or triethylenetetramine solution, with or, in particular, without the addition of an alkali or alkaline earth. These also include the isotatic zeolites according to European Pat. Nos. 34,727 and 46,504. Such borosilicate zeolites can also be prepared if the reaction is carried out in ether solution, eg. diethylene glycol dimethyl ether, or in alcoholic solution, eg. hexane-1,6-diol, instead of in aqueous amine solution.

The iron silicate zeolite is obtained, for example, from an iron compound, preferably $Fe_2(SO_4)_3$ and a silicon compound, preferably finely divided silica, in aqueous amine solution, in particular 1,6-hexanediamine, with or without the addition of an alkali or alkaline earth, at from 100° to 200° C. under autogenous pressure.

The borosilicate and iron silicate zeolites prepared in this manner can be isolated, dried at from 100° to 160° C., preferably 110° C., and calcined at from 450° to 550° C., preferably 500° C., and then molded with a binder in a weight ratio of from 90:10 to 40:60 to give extrudates or pellets. Suitable binders are various aluminas, preferably boehmite, amorphous aluminosilicates having an $SiO_2/Al_2O_3$ ratio of from 25:75 to 90:5, preferably 75:25, silica, preferably finely divided $SiO_2$, mixtures of finely divided $SiO_2$ and finely divided $Al_2O_3$, $TiO_2$, $ZrO_2$ and clay. After the molding procedure, the extrudates or pellets are dried at 110° C. for 16 hours and calcined at 500° C. for 16 hours.

Advantageous catalysts are also obtained if the iron silicate or borosilicate zeolite isolated is molded directly after drying and is not subjected to calcination until after the molding procedure. The iron silicate and borosilicate zeolites prepared can be used in pure form, without a binder, as extrudates or pellets, examples of extrusion or peptizing assistants employed being ethylcellulose, stearic acid, potato starch, formic acid, oxalic acid, acetic acid, nitric acid, ammonia, amines, silicoesters and graphite and mixtures of these.

If, because of its method of preparation, the zeolite is present not in the catalytically active, acidic H form but, for example, in the Na form, the latter can be converted completely or partially to the desired H form by ion exchange, for example with ammonium ions, and subsequent calcination, or by treatment with an acid.

If, when the zeolite catalysts are used according to the invention, deactivation due to coking occurs, it is advisable to regenerate the zeolites by burning off the coke deposit with air or with an air/N₂ mixture at from 400° to 550° C., preferably 500° C. As a result, the zeolites regain their initial activity.

By precoking, it is possible to adjust the activity of the catalyst to give optimum selectivity with respect to the desired reaction product.

In order to obtain very high selectivity, high conversions and long catalyst lives, it is advantageous to modify the zeolites. In a suitable method of modifying the catalysts, for example, the unmolded or molded zeolite is doped with metal salts by ion exchange or impregnation. The metals used are alkali metals, such as Li, Cs or K, alkaline earth metals, such as Mg, Ca or Sr, metals of main groups 3, 4 and 5, such as Al, Ga, Ge, Sn, Pb or Bi, transition metals of subgroups 4–8, such as Ti, Zr, V, Nb, Cr, Mo, W, Mn, Re, Fe, Ru, Os, Co, Rh, Sr, Ni, Pd or Pt, transition metals of subgroups 1 and 2, such as Cu, Ag or Zn, and rare earth metals, such as La, Ce, Pr, Nd, Er, Yb and U.

The doping procedure is advantageously carried out as follows: the molded zeolite is initially taken in a riser tube and an aqueous or ammoniacal solution of a halide or nitrate of the metals described above is passed over at from 20° to 100° C. Ion exchange of this type can be carried out on the hydrogen, ammonium and alkali metal form of the zeolite. In another possible method of applying metals to the zeolite, the zeolite material is impregnated with, for example, a halide, a nitrate or an oxide of the metals described above in aqueous, alcoholic or ammoniacal solution. Both ion exchange and impregnation are followed at least by a drying procedure or alternatively repeated calcination.

In a possible embodiment, for example, $Cu(NO_3)_2 \cdot H_2O$ or $Ni(NO_3)_2 \cdot 6H_2O$ or $Ce(NO_3)_3 \cdot 6H_2O$ or $La(NO_3)_2 \cdot 6H_2O$ or $Cs_2CO_3$ is dissolved in water, and this solution is used to impregnate the molded or unmolded zeolite for a certain time, for example 30 minutes. Any supernatant solution is freed from water in a rotary evaporator. Thereafter, the impregnated zeolite is dried at about 150° C. and calcined at about 550° C. This impregnation process can be carried out several times in succession in order to obtain the desired metal content.

It is also possible to prepare an aqueous $Ni(NO_3)_2$ solution or ammoniacal $Pd(NO_3)_2$ solution and to suspend the pure zeolite powder therein at from 40° to 100° C. for about 24 hours, while stirring. The product is filtered off, dried at about 150° C. and calcined at about 500° C., after which the zeolite material obtained in this manner can be further processed with or without a binder to give extrudates, pellets or fluidizable material.

The zeolite in the H form can be subjected to ion exchange as follows: the zeolite, in the form of extrudates or pellets, is initially taken in a column, and, for example, an aqueous $Ni(NO_3)_2$ solution or ammoniacal $Pd(NO_3)_2$ solution is circulated over the said zeolite at slightly elevated temperatures of from 30° to 80° C. for from 15 to 20 hours. Thereafter, the zeolite is washed thoroughly with water, dried at about 150° C. and calcined at about 550° C. In the case of some metal-doped zeolites, for example Pd-doped, Cu-doped or Ni-doped zeolites, an aftertreatment with hydrogen is advantageous.

In another possible method of modification, the molded or unmolded zeolite material is subjected to a treatment with an acid, such as hydrochloric acid, hydrofluoric acid or phosphoric acid, and/or steam. This is advantageously done, for example, by treating the zeolite in powder form with 1N phosphoric acid for 1 hour at 80° C. After the treatment, the product is washed with water, dried at 110° C. for 16 hours and calcined at 500° C. for 20 hours. In another procedure, the zeolite, before or after it has been molded with a binder, is treated with a 3–25, in particular 12–20, % strength by weight aqueous hydrochloric acid, for example for from 1 to 3 hours at from 60° to 80° C. The zeolite treated in this manner is then washed with water, dried, and calcined at from 400° to 500° C.

In a particular embodiment of the acid treatment, the zeolite material, before being molded, is treated at elevated temperatures with hydrofluoric acid, which is generally used in the form of 0.001–2N, preferably 0.05–0.5N, hydrofluoric acid, for example by refluxing for, in general, from 0.5 to 5, preferably from 1 to 3, hours. After the zeolite material has been isolated, for example, by being filtered off and washed thoroughly, it is advantageously dried, for example at from 100° to 160° C., and calcined at in general from 450° to 600° C. In another preferred embodiment of the acid treatment, the zeolite material is molded with a binder and then treated at elevated temperatures, advantageously at from 50° to 90° C., preferably from 60° to 80° C., for from 0.5 to 5 hours, preferably with from 12 to 20% strength by weight hydrochloric acid. The zeolite material is advantageously then washed thoroughly, dried at from 100° to 160° C. and calcined at from 450° to 600° C. An HF treatment can also be followed by an HCl treatment.

In another procedure, zeolites can be modified by applying phosphorus compounds, such as trimethoxyphosphate, trimethoxyphosphine or primary, secondary or tertiary sodium phosphate. The treatment with primary sodium phosphate has proven particularly advantageous. In this procedure, the zeolites, in the form of extrudates, pellets of fluidizable material, are impregnated with aqueous $NaH_2PO_4$ solution, dried at 110° C. and calcined at 500° C.

The catalysts can alternatively be used in the form of 2–4 mm extrudates, tablets of 3–5 mm diameter or powders having particle sizes of 0.1–0.5 mm or as a fluidizable catalyst.

The conversion is preferably carried out in the gas phase at from 200° to 550° C., in particular from 300° to 450° C., and at a WHSV of from 0.1 to 20 $h^{-1}$, in particular from 0.5 to 5 $h^{-1}$ (g of starting material per g of catalyst per hour), in a fixed bed or fluidized bed. In general, the conversion increases sharply wtih increasing temperature, while the selectivity decreases only slightly within a certain temperature range. The reaction can also be carried out in the liquid phase (suspension, trickle-bed or liquid phase method). As a rule, the process is effected uner atmospheric or superatmospheric pressure and preferably continuously, although it may also be carried out by a batchwise procedure.

Sparingly volatile or solid starting materials are used in dissolved form, for example in solution in water, tetrahydrofuran, toluene or petroleum ether. In general, dilution with solvents or inert gases, such as $N_2$ or Ar, is also possible.

After the reaction, the resulting 1,4-diazabicyclo[2.2.2]octanes are isolated from the reaction mixture by a conventional method, for example by distillation; unconverted starting materials may be recycled to the reaction.

EXAMPLES 1 TO 8

The reaction is carried out under isothermal conditions in a tube reactor (0.6 cm coil, 90 cm length) in the gas phase for not less than 6 hours. Separation and characterization of the reaction products are carried out by conventional methods. Quantitative determination of the reaction products and the starting materials is effected by gas chromatography.

The catalysts used in the examples are:

Catalyst A

A borosilicate zeolite of the pentasil type is prepared in a hydrothermal synthesis from 640 g of finely divided $SiO_2$, 122 g of $H_3BO_3$ and 8 kg of an aqueous 1,6-hexanediamine solution (weight ratio 50:50) at 170° C. under autogenous pressure in a stirred autoclave. The crystalline reaction product is filtered off, washed thoroughly, dried at 100° C. for 24 hours and calcined at 500° C. for 24 hours. This borosilicate zeolite is composed of 94.2% by weight of $SiO_2$ and 2.3% by weight of $B_2O_3$.

This material is converted to 2 mm extrudates by molding with a molding assistant, and the extrudates are dried at 110° C. for 16 hours and calcined at 500° C. for 24 hours.

Catalyst B

An iron silicate zeolite of the pentasil type is synthesized under hydrothermal conditions, under autogenous pressure and at 165° C., from 273 g of waterglass, dissolved in 253 g of an aqueous 1,6-hexanediamine solution (weight ratio 50:50) and 31 g of iron sulfate, dissolved in 21 g of 96% strength sulfuric acid and 425 g of water, in a stirred autoclave in the course of 4 days. The zeolite is filtered off, washed thoroughly, dried at 110° C. for 24 hours and calcined at 500° C. for 24 hours. The iron silicate zeolite obtained has an $SiO_2/Fe_2O_3$ ratio of 17.7 and an $Na_2O$ content of 1.2% by weight. The catalyst is extruded with finely divided $SiO_2$ in a weight ratio of 80:20 to give 2.5 mm extrudates, which are dried at 110° C. for 16 hours and calcined at 500° C. for 24 hours.

Catalyst C

Catalyst C is obtained by impregnating catalyst A with a $Pd(NO_3)_2/Ce(NO_3)_3$ solution. After the product has been dried at 130° C. for 2 hours and calcined at 540° C. for 2 hours, the Pd content is 1.3% by weight and the Ce content 3.6% by weight.

Catalyst D

Catalyst D is obtained by molding the borosilicate zeolite described under catalyst A with finely divided $SiO_2$ in a weight ratio of 70:30 to give 2 mm extrudates, drying the latter at 110° C. for 16 hours and calcining them at 500° C. for 16 hours. These extrudates are impregnated with an aqueous $NaH_2PO_4$ solution, dried at 110° C. and calcined at 500° C. for 14 hours. The Na content is 5% by weight and the P content 7.5% by weight.

Catalyst E (comparison catalyst)

A ZSM 5 aluminosilicate zeolite is synthesized as described in U.S. Pat. No. 3,702,886, Example 1. This ZSM 5 zeolite is molded with boehmite in a weight ratio of 60:40, dried at 110° C. and calcined at 500° C. for 16 hours. The extrudates are subjected to ion exchange with 20% strength $NH_4Cl$ solution by a conventional method at 80° C. for 2 hours, after which the Na content is 0.02% by weight (after drying at 110° C. and calcination at 500° C. for 5 hours).

The experimental results obtained with the catalysts described above are listed in Table 1 below.

Starting solution I: monohydroxyethylpiperazine dissolved in water in a ratio of 25 g to 75 g.

Starting solution II: Mixture of mono- and dihydroxyethylpiperazine (weight ratio 20:80) dissolved in water in a ratio of 25 g :75 g

TABLE 1

|  | Example | | | | | | | |
|---|---|---|---|---|---|---|---|---|
|  | 1 | 2 | 3 | 4 | 5* | 6 | 7 | 8 |
| Starting solution | I | I | I | I | I | II | II | II |
| Catalyst | A | B | C | D | E | A | C | D |
| Temperature | 400° C. | 400° C. | 400° C. | 400° C. | 400° C. | 400° C. | 400° C. | 400° C. |
| WHSV | $1.5\,h^{-1}$ | $1.5\,h^{-1}$ | $1.5\,h^{-1}$ | $3\,h^{-1}$ | $2\,h^{-1}$ | $1.5\,h^{-1}$ | $2\,h^{-1}$ | $2\,h^{-1}$ |
| Conversion % | 98.9 | 99.7 | 99.7 | 99.9 | 99.6 | 99.8 | 99.6 | 99.8 |
| Selectivity % | | | | | | | | |
| DABCO | 65.6 | 73.5 | 76.8 | 83.2 | 68.5 | 68.3 | 67.8 | 84.9 |
| Piperazine | 7.3 | 10.3 | 5.9 | 9.9 | 12.4 | 9.4 | 6.5 | 3.9 |

*Comparative example

We claim:

1. A process for the preparation of 1,4-diazabicyclo-[2.2.2]octane of a C-substituted 1,4-diazabicyclo[2.2.2]-octane of the formula (I)

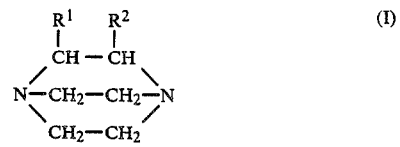

where $R^1$ and $R^2$ are each hydrogen or alkyl or alkenyl, each of 1 to 4 carbon atoms, wherein a heterocyclic amine of the formula (II)

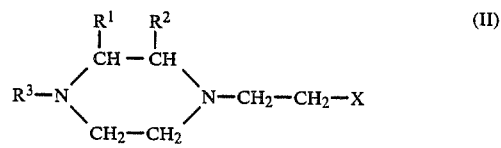

where $R^1$ and $R^2$ have the above meanings, $R^3$ is hydrogen, hydroxyethyl or aminoethyl and X is hydroxyl or amino, is converted in the presence of borosilicate and-/or iron silicate zeolites as catalysts.

2. The process of claim 1, wherein monohydroxyethylpiperazine or dihydroxyethylpiperazine or a mixture of these is used as a starting material.

3. The process of claim 1, wherein the catalyst used is a zeolite of the pentasil type.

4. The process of claim 1, wherein the catalyst used is a borosilicate zeolite of the pentasil type.

5. The process of claim 1, wherein the catalysts used are borosilicate and/or iron silicate zeolites modified with rare earth metals and/or transition metals and/or alkali metals and/or alkaline earth metals and/or phosphorus compounds.

* * * * *

UNITED STATES PATENT AND TRADEMARK OFFICE
CERTIFICATE OF CORRECTION

PATENT NO. : 4,804,758
DATED : February 14, 1989
INVENTOR(S) : Hoelderich et al.

It is certified that error appears in the above-identified patent and that said Letters Patent is hereby corrected as shown below:

On the title page, under item [22], insert

[30] Foreign Application Priority Data

Oct. 8, 1986 (DE)  Fed. Rep. of Germany ..... 3634261

IN the Claims:

Claim 1, Column 6, Line 41

"of a C-substituted"

Should be:

"or a C-substituted"

Signed and Sealed this

Thirtieth Day of April, 1991

Attest:

HARRY F. MANBECK, JR.

Attesting Officer

Commissioner of Patents and Trademarks